United States Patent [19]

Horvath

[11] Patent Number: 4,795,474
[45] Date of Patent: Jan. 3, 1989

[54] ROTARY JOINT ESPECIALLY FOR A KNEE PROSTHESIS

[75] Inventor: Eduard Horvath, Vienna, Austria

[73] Assignee: Otto Bock Orthopädische Industrie Besitz - und Verwaltungs-KG, Duderstadt, Fed. Rep. of Germany

[21] Appl. No.: 927,729

[22] Filed: Nov. 5, 1986

[30] Foreign Application Priority Data

Nov. 6, 1985 [AT] Austria .................................. 3204/85

[51] Int. Cl.4 .............................................. A61F 2/74
[52] U.S. Cl. ...................................... 623/27; 623/43; 623/39; 623/59
[58] Field of Search ....................... 623/27, 39, 43, 44, 623/46, 47, 48, 18, 20; 403/78, 164, 165; 16/326, 332

[56] References Cited

U.S. PATENT DOCUMENTS

| | | | |
|---|---|---|---|
| 1,008,048 | 11/1911 | Mueller | 623/27 X |
| 2,594,533 | 4/1952 | Baker | 16/326 |
| 2,866,673 | 12/1988 | Van Der Knoop | 403/164 X |
| 3,172,127 | 3/1965 | Tolotti | 623/44 |
| 3,538,516 | 11/1970 | Bailey et al. | 623/43 X |
| 3,837,010 | 9/1974 | Prout | 623/43 X |
| 3,956,775 | 5/1976 | Moore | 623/27 X |
| 4,023,215 | 5/1977 | Moore | 623/43 |
| 4,186,449 | 2/1980 | Horvath | 623/27 |
| 4,308,419 | 12/1981 | Fredriksson | 403/78 X |
| 4,351,070 | 9/1982 | Blatchford | 623/44 |
| 4,619,660 | 10/1986 | Christiansen et al. | 623/46 |

Primary Examiner—Richard J. Apley
Assistant Examiner—Howard Flaxman
Attorney, Agent, or Firm—Herbert Dubno

[57] ABSTRACT

A rotary joint, especially for a prosthesis, e.g. to allow a user to assume the lotus position, as a pair of relatively rotating parts including an outer part and an inner part braced at coaxial bosses by tapered rollers forming a play-eliminating tapered roller bearing. An inclined roller bearing is provided between outer peripheries of disk portions of these parts. A housing enclosing the parts contains a locking device in which a locking element is spring biased to engage the parts with teeth of the locking element engaging in teeth of the two parts. A push-button can be depressed to retract the locking element and permit relative rotation.

17 Claims, 7 Drawing Sheets

ROTARY JOINT ESPECIALLY FOR A KNEE PROSTHESIS

FIELD OF THE INVENTION

My present invention relates to a rotary joint, especially for a prosthesis which is to be subjected to high tilting forces in a direction transverse to the axis of relative rotation of two substantially disk-shaped parts adapted to be attached to the relatively displaceable members of the prosthesis connected by the joint.

BACKGROUND OF THE INVENTION

In Eastern cultures and, increasingly, in Western cultures, individuals may frequently desire to assume the so called lotus position which provides a particular stress on the knee joints since it requires a crossing of the legs when they are bent beneath or close to the body of the individual.

If a joint for a prosthesis is to be able to withstand the folding of the legs to permit assumption of the lotus position, this joint must be able, in addition to permitting relative rotation of the upper and lower leg members connected by the joint, to withstand exceptionally high tilting forces. The joint which thus can connect the knee articulation to the upper leg, for example, must be constructed to withstand these very high tilting forces since these joints must bear the entire weight of the individual using the prosthesis.

OBJECTS OF THE INVENTION

It is the principal object of my present invention, therefore, to provide a rotary joint for a prosthesis which can absorb without play in the relatively rotatable parts, such tilting forces and yet not be of dimensions which preclude incorporation of the joint in the prosthesis.

Another object of this invention is to provide a rotary joint which can be positioned with a knee articulation and another member of a prosthesis, which can allow the individual using the prosthesis to assume a lotus position without difficulty but which nevertheless, in a structure of comparatively small size, is capable of absorbing without play the high tilting forces which may be generated in such action.

It is also an object of this invention to provide a high strength play-free rotary joint which is of low weight and small size but has a high degree of reliability and long useful life.

SUMMARY OF THE INVENTION

These objects and others which will become apparent hereinafter are attained, in accordance with the invention by providing both of the relatively rotatable parts, namely, an inner part and an outer part so that each has a central tubular boss with the tubular boss of the inner part being received with all-around clearance in the tubular boss of the outer part so that the bosses are coaxial.

The outer peripheries of the disk portions of the relatively rotatable parts are braced against one another by antifriction means while the bosses receive between them tapered rollers so that these tapered rollers form with the bosses a tapered-roller bearing. The transition between each boss and the respective disk portion is located at the small-diameter end of the tapered roller bearing.

In this manner, the tilting movement which may be applied to the joint is also taken up by two bearings, namely, the tapered roller bearing previously described and the bearings rotatably bracing the outer peripheries of the disk portions against one another. The force transmitting portions of the rotary parts are always under compression, thereby avoiding alternating stress on the rotating parts.

To maintain the two parts without play, means is provided for preventing the tapered rollers from falling out of the annular clearance between the bosses, this means, preferably in the form of a cover or disk having a shank threaded held in the inner part, engaging over the outer large-diameter ends of the tapered rollers and pressing them into place.

The bracing means between the outer peripheries of the disk portions of the relatively rotatable parts can be formed by a slide or plain bearing or a roller bearing, preferably a ball bearing and most advantageously an inclined or self-aligning ball bearing.

In the latter case, the ball bearing functions together with the tapered roller bearing to ensure easy relative rotation of the two parts and hence rotation of the joint in spite of the elimination of play therein.

According to a feature of the invention, both relatively rotatable parts are received in a housing which can be provided with a device for locking the relatively rotatable parts with respect to one another so that the joint can have general utility in addition to the specific utility of enabling the user to assume the lotus position.

According to a feature of the invention, therefore, the locking device can include a locking element displaceable in the housing radially of the aforementioned axis and the relatively rotatable parts and which can be displaced into respective recesses formed on these parts or retractable from the recesses to permit relative rotation.

The locking element on its end engageable in the recesses of the rotating parts can have teeth of different shapes on opposite sides of the engaging end for interdigitation with corresponding counter teeth formed in the respective recesses. The locking of the parts together by interdigitating sets of teeth ensures that the forces which must be absorbed by the locking means will be spread over a multiplicity of contacting surfaces, namely, the flanks of the teeth.

Because of the different tooth configurations on opposite sides of the locking element, the teeth which are turned toward the part fixed with respect to the housing can have its tooth flanks parallel to radial planes of the relatively rotatable parts while the teeth on the opposite side of the locking element can be inclined toward the leading end thereof in the direction of the teeth on the fixed part. This allows the teeth flanks which are parallel to the radial plane to be in permanent engagement even upon partial retraction of the locking element while releasing the rotating one of the parts for such rotation even with a comparatively small retraction movement of the locking element. The teeth of the locking element, therefore, form guide members for the latter as well.

According to another feature of the invention for guiding the locking element, the latter can be formed at its end opposite its toothed end, with a pair of parallel opposing projections which extend parallel to the direction of displacement of the locking element as well and flank opposite sides of a guide pin, thereby guiding the locking element at both ends and assuring an especially firm, play-free retention of the relatively rotatable parts in their locked position.

For actuating the locked element, I can provide a push-button which is displaceable in the housing and operates the locking element via at least one rocker lever. With this arrangement an especially simple retraction of the locking element from the recesses of the relatively rotating parts can be achieved.

To prevent jamming of the locking element, I can provide two such rocker levers in symmetrical relationship and preferably two rocker lever pairs on opposite sides of the locking element, these rocker levers being swingable on a common pin fixed to the locking element. The levers extend in opposite directions away from this pin and have free ends which are formed with slide slots opening outwardly and extending transversely to the direction of displacement of the push-button and in which pins of the push-button engage so that displacement of the push-button results in a corresponding displacement of the free ends of the rocker levers. The rocker levers can engage abutment surfaces with their outer edges and upon rocking movement can row on these abutment surfaces.

Preferably upon depression of the push-button to retract the locking element, the rotating surfaces of the rocking levers can ride against the guide bolt for the locking element whereby other support surfaces are rendered superfluous.

For an automatic displacement of the locking element into the recess, i.e. self-locking of the device, the latter can be spring loaded to bring the teeth of the locking element into interdigitation with the teeth of the relatively rotating members.

The means for spring loading the locking element can include compression coil springs acting symmetrically on the rocker levers at their free ends and a relatively high degree of prestress can be applied by the spring elements to avoid tilting of the locking element.

The spring elements themselves can be telescoping legs whose telescopingly engageable members are braced apart by the prestressed coil springs and themselves are supported in the housing and pivotally connected to the pin engaging the free ends of the respective rocker levers.

BRIEF DESCRIPTION OF THE DRAWING

The above and other objects, features and advantages of my invention will become more readily apparent from the following description, reference being made to the accompanying highly diagrammatic drawing in which.

SPECIFIC DESCRIPTION

Figure 1:
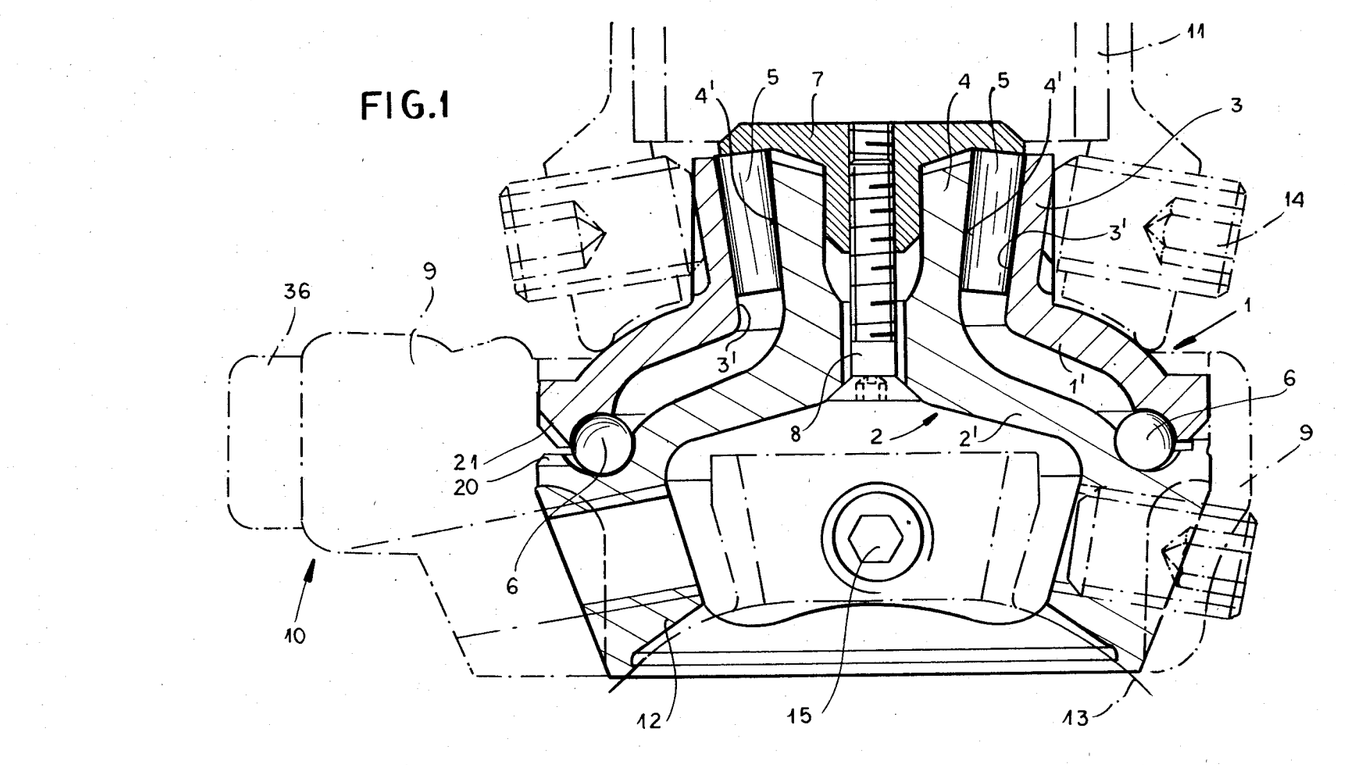
FIG. 1 is an axial cross sectional view through the point of the invention.

The rotary joint of the invention, which can be interposed between a prosthetic knee joint and the upper limb, for example, can comprise two disk-shaped relatively rotatable parts 1, 2, each of which is formed with a central boss 3 such that the boss 3, 4 of one of the rotary parts 1 receives concentrically the boss 4 of the other rotary part 2. The outer wall 4' of the inner boss 4 is thereby spaced from the inner wall 3' of the outer boss 3 so that the two walls 3', 4' form the races for the roller bodies 5 of a tapered roller bearing whose small diameter end is located at the transition between the disk portions 1', 2' and the respective basis 3, 4 of the parts 1 and 2. The second rotary bracing of the parts 1 and 2 with respect to one another is effected in the peripheral region of the disk portions 1', 2' via an inclined ball bearing 6. This combination of the two bearings ensures a completely play free journaling of the two parts 1, 2 relative to one another, especially since any play can be eliminated by ensuring that the tapered rollers 5 are held sufficiently deeply in the annular clearance between the surfaces 3' and 4'.

The tapered rollers 5 are pressed to a variable degree into the clearance with the surfaces 3', 4' to regulate the degree to which play is taken up, by a cap 7 having a disk portion overhanging the large diameter ends of the tapered rollers 5 and bearing thereon, a shank of this cap being threadedly engaged by a screw 8 traversing the central bore of the inner boss 4 and which can be tightened to draw the cap 7 against the roller bodies 5.

The cap 7 and the screw 8 thus also hold the bearing rollers in place and because the surfaces 3' and 4' are tapered, the rollers 5 serve to prevent the part 1 from falling off of the part 2.

The pressure applied by the cap 7 to the tapered rollers 5 also has an axial force component applied to the outer part 1 to press the latter against the balls of the inclined ball bearing 6 so that play is also excluded in the outer peripheral region of the relatively rotatable parts 1 and 2.

The described combination and arrangement of the bearings and the means for taking up play therein assure not only that relative rotation is permitted between the members to which these parts 1 and 2 are connected, but also that the joint is able to take up very high forces without play.

The two relatively rotatable parts 1 and 2 are received in a housing 9 which peripherally surrounds these parts and in which a locking device 10 is provided. The outer side of the boss 3 of part 1 is provided with means, e.g. utilizing socket-type set screws 14, for connecting the joint to one member 11 of the prosthesis, e.g. the upper member of a leg prosthesis.

The rotatable part 2 has a connecting socket for a projecting prosthesis portion 13 which can be anchored in place by the socket set screws 15, the latter prosthesis part being, for example, a standard knee joint.

Figure 2:
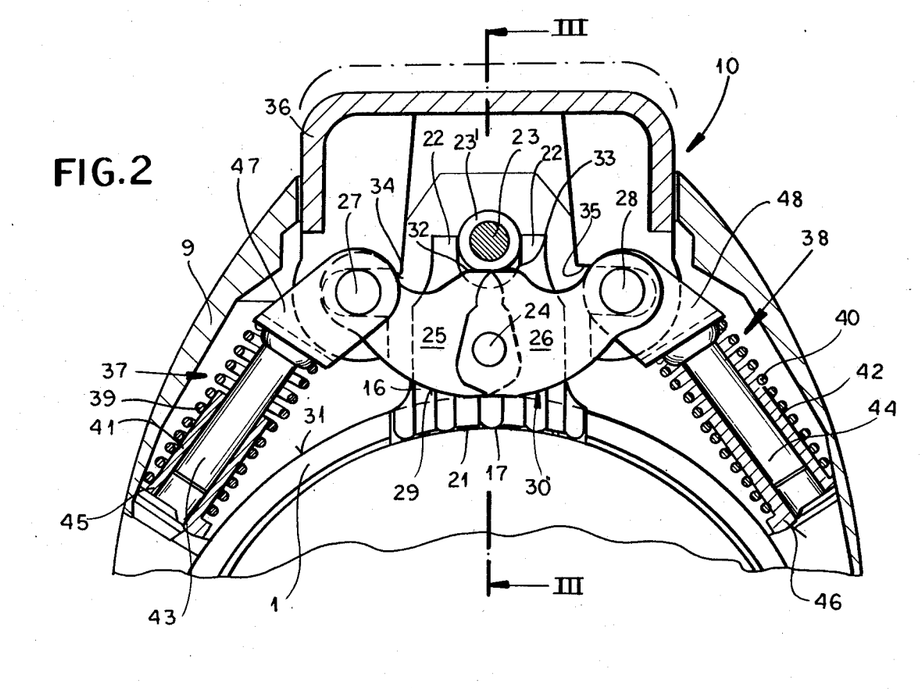
FIG. 2 is a radial section through the locking device thereof taken along the line II—II of FIG. 3 showing the device in the locked position.

The locking device 10 comprises a locking element 16 which is shiftable in a radial direction with respect to the relatively rotatable parts 1 and 2.

On an end 17 of the locking element 16 turned toward the parts 1 and 2, the element 16 is provided with arrays of teeth 18 and 19 which differ from one another on the two sides of the locking element 16. The array of teeth 19, seen from above in FIG. 2, are engageable in teeth 21.

The teeth 18 turn toward the part 2 which is fixed with respect to the housing 9, has toothed flanked 18' which are parallel to radial plains of the parts 1 and 2 whereas the toothed flanks 19' are inclined in the direction toward the end 17 and toward the teeth 18.

Figure 9:
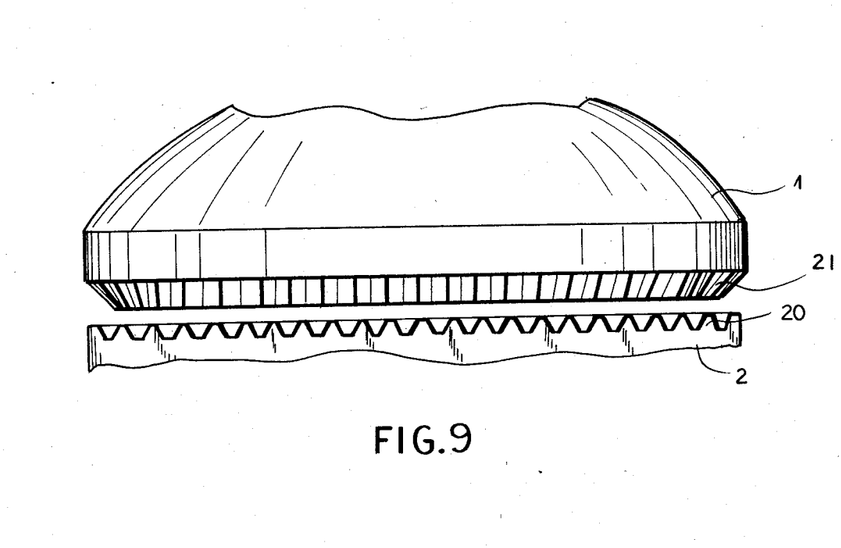
FIG. 9 is a fragmentary side elevation showing the teeth on the two relatively rotatable parts.

The part 2 is formed with teeth 20 complementary to the teeth 18 and interdigitated therewith while the part 1 has teeth 21 complementary to the teeth 19 and interdigitating therewith.

At the end of the locking element 16 opposite that provided with the teeth 18 and 19, this locking element is provided with two parallel but opposing projections 22 which flank a guide pin 23 and can ride against guide sleeves 23' on this pin.

Figure 6:
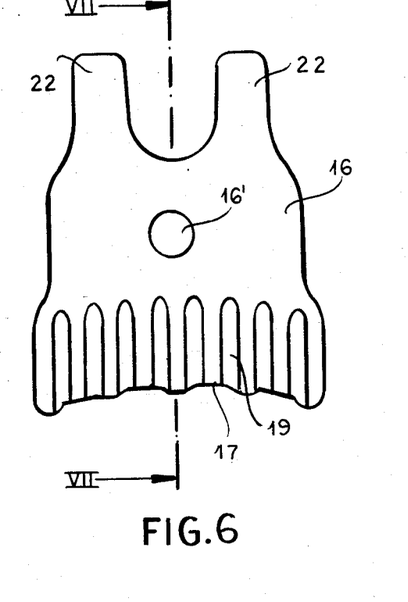
FIG. 6 is an elevational view of the locking element.
Figure 7:
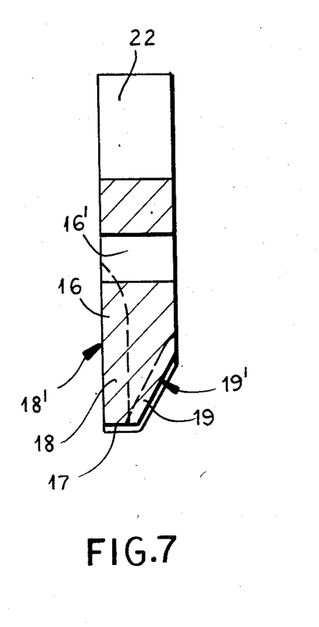
FIG. 7 is a section taken along VII—VII of FIG. 6.
Figure 8:
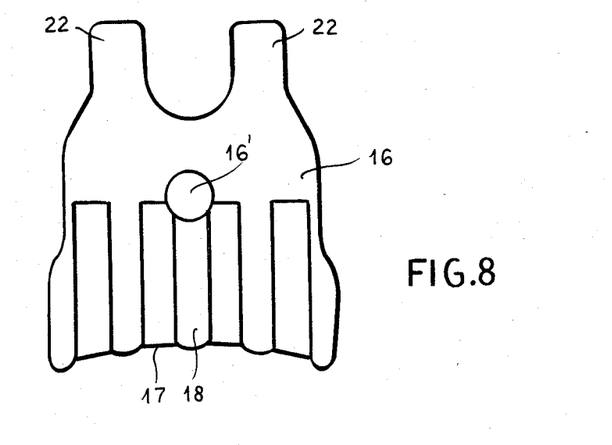
FIG. 8 is an elevational view of the locking element of FIG. 6 seen from the opposite side.

The locking element 16 has a bore 16' in which is received (FIGS. 6–8) a bearing pin 24 upon which four rocker levers 25, 26 are pivotally mounted. These rocker levers are provided in two pairs with the rocker levers of each pair extending laterally at their free ends beyond the locking element 16 and one of the pairs being provided along each face of the locking element 16 (compare FIGS. 4 and 5, for example).

Figure 4:
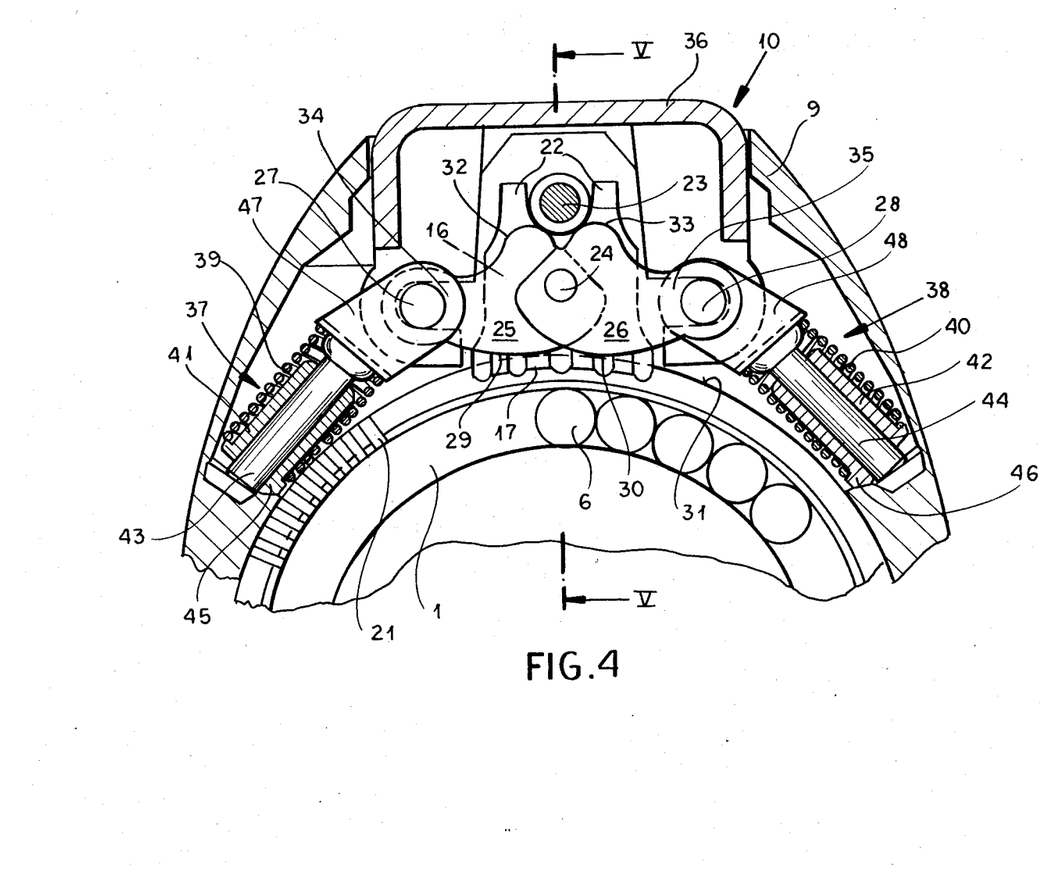
FIG. 4 is a view similar to FIG. 2 but illustrating the unlocked position of the device.

The rocker levers 25, 26 of each pair, therefore, swing in opposite senses and have their free ends connected to respective pins 27, 28, the pins coupling the corresponding free ends of the rocker levers of the two pairs.

The contours of the rocker levers 25, 26 are so arranged that with their outer edges 29, 30 turned toward the parts 1 and 2 they can roll upon the outer edge 31 of one or both of these relatively rotatable parts.

The outer contours 32, 33 of the rocker levers which are likewise mounted and turn away from the parts 1 and 2 can ride upon the sleeves 23' of the guide bolt 23 previously described.

The pins 27, 28 engaging the free ends of the rocker levers 25, 26 ride in guide slots 34, 35 which are formed in a push-button 36 and extend therein in a direction transverse to the direction of displacement of the locking element 16.

Eyes 47 an 48 are connected to the inner members 43, 44 of respective telescoping spring assemblies 37 and 38 which urge the free ends of the levers 25, 26 as seen in FIG. 4 respectively in the clockwise and in the counterclockwise sense, tending to urge the push-button 36 outwardly and simultaneously spring bias the locking element 16 into locking engagement with the parts 1 and 2.

Each of these telescoping spring arrangements includes an outer sleeve member 41, 42 receiving the rod-like inner member 43, 44.

At one end each of the prestress compression coil springs 39, 40 is braced against the sleeve 41 or 42 and is seated at its opposite end against the respective eye 47, 48.

Figure 3:
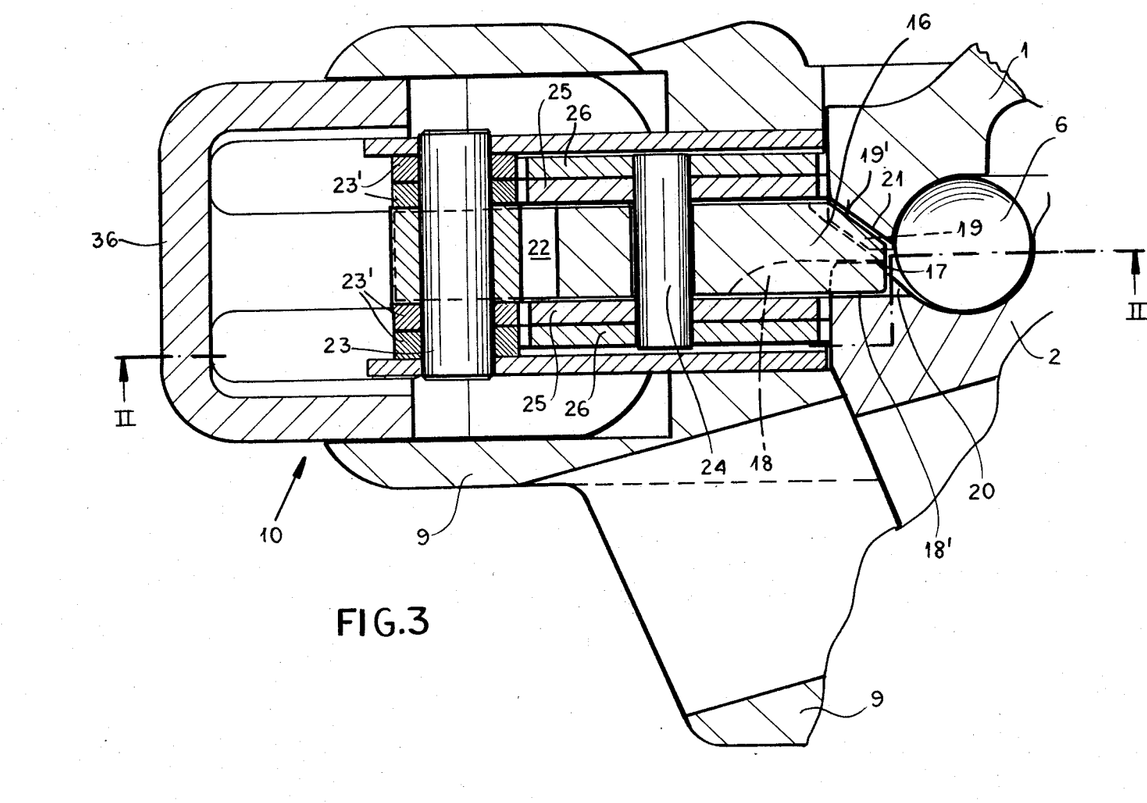
FIG. 3 is a section taken along the line III—III of FIG. 2.

In its normal use position best seen in FIGS. 2 and 3, the push-button projects outwardly from the housing and the locking element 16 engages with its teeth 18 in the recesses 20 of part 2 and with its teeth 19 in the recesses 21 of the part 1.

The rotary parts are locked together and, for example, assumption of the lotus position by rotating the lower leg prosthesis members inwardly is not permitted.

However, when the push-button 36 is depressed, to enable relative rotation of the parts 1 and 2, the pins 27 and 28 are displaced toward the rotating parts, causing the rocker levers 25, 26 to swing as the arcuate portions 29 and 30 ride on the edge 31 previously mentioned.

Figure 5:
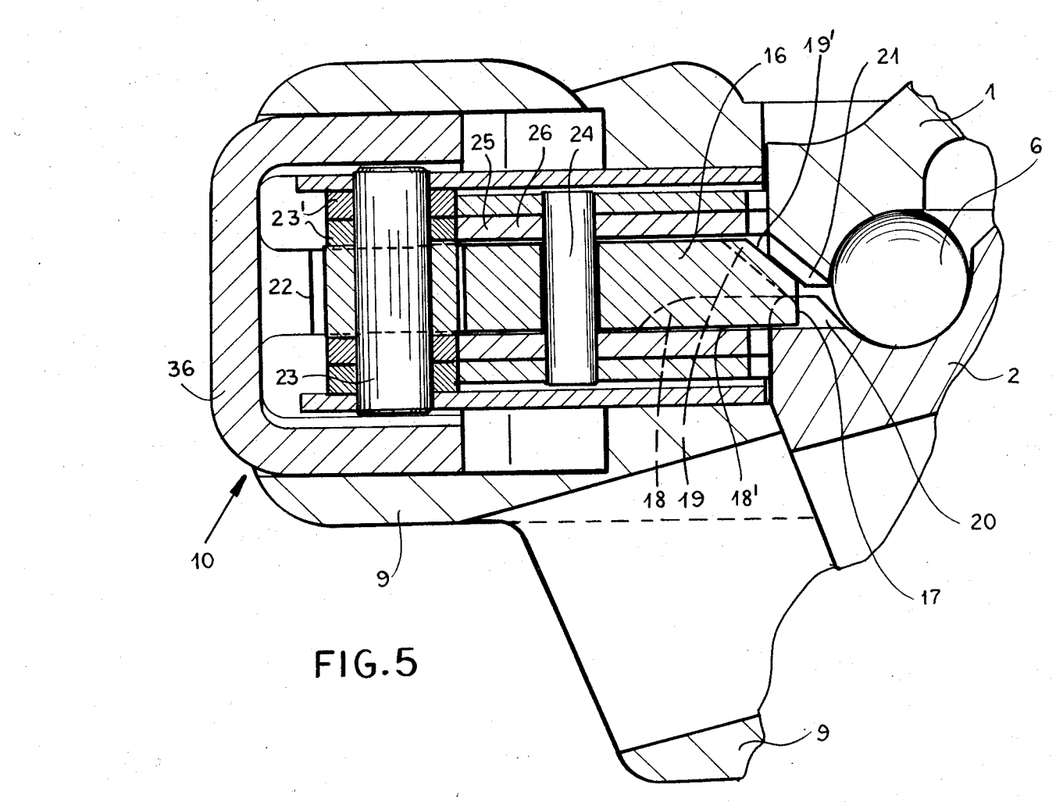
FIG. 5 is a section along the line IV—IV of FIG. 4.

This causes the pin 24 to move radially away form the parts 1 and 2, thereby withdrawing the teeth 19 from the recess 21 permitting relative rotation of the parts. The springs 37, 38 are further compressed. In FIGS. 4 and 5 I have shown the position of the device when the push-button 36 is fully depressed. The movement of the locking element is limited by the engagement of the base of the notch between the projections 22 against the guide pin 23.

As is apparent from FIG. 5, in this position the teeth 18 can remain interdigitated with the teeth of the recesses 20 although the teeth 19 are fully retracted from recesses 21 so that a rotation of the rotatable part 1 relative to the part 2 is possible.

Upon release of the push-button 36, the telescoping spring units 37 and 38 are effective automatically to move the pins 27 and 28 away from the parts 1 and 2. The outer edges 32 and 33 thereby ride upon the guide pin 23 and tend to move the pin 24 toward the centrum of the parts 1 and 2. However, if the parts 1 and 2 have been relatively rotated to disalign the recesses 20 and 21, the leading end 17 of the locking element 16 will come to rest against the outer surface of the part 1 and prevent further movement of the locking element in the locking direction.

Once the user has swung the lower limbs out of the lotus position, therefore, and the rotating part 1 has been returned to its starting position, the recesses 20 and 21 are again aligned so that the locking element 16 can spring into the locking position with the teeth 19 engaging in the recesses 21 under the action of the spring units 37, 38 automatically. The joint is then again locked and the parts can be found in the position shown in FIGS. 2 and 3.

I claim:

1. A rotary joint, especially for a prosthesis, adapted to withstand high tilting forces transverse to an axis of relative rotation of two members to be connected by the joint, said rotatable joint comprising:
    an outer part formed with a disk portion and a central boss connected to said disk portion at a transition region between said boss and said disk portion;
    an inner part formed with a disk portion juxtaposed with said disk portion of said outer part, and a central boss coaxial with said central boss of said outer part along said axis and received therein, said central boss of said inner part being connected to said disk portion of said inner part at a respective transition region between said boss and said disk portion of said inner part;
    an array of tapered bearing rollers received between said bosses and defining therewith a tapered-roller bearing having a small diameter end substantially at said transition regions;
    means for bracing outer peripheries of said disk portions rotatably against one another;
    means for connecting each of said parts to a respective member so that said members have an axis of relative rotation and are connected to said joint, and a locking device for locking said inner and outer parts against rotation relative to said locking device including a locking element movable relative to said inner and outer parts radially thereof, said inner and outer parts being formed with recesses adapted to receive said locking element for immobilizing said parts against relative rotation, said parts being relatively rotatable upon retraction of said element radially from said recesses.

2. The joint defined in claim 1 wherein said means for bracing outer peripheries of said disk portions rotatably against one another includes a plain slide bearing.

3. The joint defined in claim 1 wherein said means for bracing outer peripheries of said disk portions rotatably against one another includes an array of balls forming with said disk portions a ball bearing.

4. The joint defined in claim 3 wherein said ball bearing is an inclined ball bearing.

5. The joint defined in claim 1, further comprising:
a housing receiving said inner and outer parts; said locking device in said housing.

6. The joint defined in claim 5 wherein said element is formed with a toothed extremity whose teeth interdigitate with teeth formed on said parts in said recesses thereof.

7. The joint defined in claim 6 wherein said housing is fixed to one of said parts, the interdigitating teeth of said element and said one of said parts having flanks parallel to a radial plane of said parts, the interdigitating teeth of the other of said parts and said element being inclined toward a leading edge of said element in the direction of the teeth of said one of said parts.

8. The joint defined in claim 7 wherein said element is guided in said housing by a pair of mutually parallel opposing projections formed on an end of said element opposite the toothed end thereof and engaging from opposite sides on a guide pin.

9. The joint defined in claim 8, further comprising a push-button slidably mounted on said housing for actuating said element, and at least one rocker lever pivotally connected to said element and displaceable by said push-button.

10. The joint defined in claim 9 wherein two rocker levers are pivotally connected to said element at a common pin fixed on said element and have free arms provided with respective pins guided in respective slots formed in said push-button and extending transversely to the direction of displacement of said push-button for displacement of said levers by actuation of said push-button.

11. The joint defined in claim 10 wherein said rocker levers have surfaces rollingly engaging at least one abutment upon pivotal movement of said rocker levers about said common pin.

12. The joint defined in claim 11 wherein upon depression of said push-button and resultant retraction of said element from engagement with said parts, said levers rollingly engage one of said parts and for insertion of said element into engagement with said parts, said levers rollingly engage said guide pin.

13. The joint defined in claim 12, further comprising spring means biasing said element into toothed engagement with said parts.

14. A rotary joint, especially for a prosthesis, comprising:
a first generally disk-shaped part centered on an axis;
a second relatively disk-shaped part juxtaposed with said first part and rotatable relative thereto;
bearing means interposed between said parts to enable relative rotation thereof;
a housing receiving said first and second parts; and
a locking device in said housing for locking said first and second parts to one another against rotation, said locking device comprising a locking element movable relative to said first and second parts radially thereof, said first and second parts being formed with recesses adapted to receive said locking element for immobilizing said parts against relative rotation, said parts being relatively rotatable upon retraction of said element radially from said recesses, said element being formed with a toothed extremity whose teeth interdigitate with teeth formed on said parts in said recesses thereof, said housing being fixed to one of said parts, the interdigitating teeth of said element and said one of said parts having flanks parallel to a radial plane of said parts, the interdigitating teeth of the other of said parts and said element being inclined toward a leading edge of said element in the direction of the teeth of said one of said parts, said element being guided in said housing by a pair of mutually parallel opposing projections formed on an end of said element opposite the toothed end thereof and engaging from opposite sides on a guide pin.

15. The joint defined in claim 14, further comprising a push-button slidably mounted on said housing for actuating said element, and at least one rocker lever pivotally connected to said element and displaceable by said push-button.

16. The joint defined in claim 15 wherein two rocker levers are pivotally connected to said element at a common pin fixed on said element and have free arms provided with respective pins guided in respective slots formed in said push-button and extending transversely to the direction of displacement of said push-button for displacement of said levers by actuation of said push-button.

17. The joint defined in claim 16 wherein upon depression of said push-button and resultant retraction of said element from engagement with said parts, said levers rollingly engage one of said parts and for insertion of said element into engagement with said parts, said levers rollingly engage said guide pin, said joint further comprising spring means biasing said element into toothed engagement with said parts.

* * * * *